United States Patent
Marzi et al.

[11] Patent Number: 5,047,433
[45] Date of Patent: Sep. 10, 1991

[54] N-ALKYL DERIVATIVES OF 2-AMINO-6,7-DIMETHOXY TETRALINE AND PHARMACEUTICAL COMPOSITIONS HAVING ANTIHYPERTENSIVE ACTIVITY CONTAINING SAME

[75] Inventors: Mauro Marzi; Maria O. Tinti; Romano Di Fabio; Domenico Misiti, all of Rome, Italy

[73] Assignee: Sigma-Tau Industrie Farmaceutiche Riunite S.p.A., Rome, Italy

[21] Appl. No.: 135,335

[22] Filed: Dec. 21, 1987

[30] Foreign Application Priority Data

Dec. 23, 1986 [IT] Italy .................. 48779 A/86

[51] Int. Cl.[5] .................. A61K 31/135; C07C 211/60; C07C 215/70
[52] U.S. Cl. .................... 514/653; 514/654; 514/657; 564/363; 564/364; 564/365; 564/381; 564/428
[58] Field of Search ............... 564/381, 428, 363, 364, 564/365; 514/653, 654, 657

[56] References Cited

U.S. PATENT DOCUMENTS

| | | | |
|---|---|---|---|
| 3,534,055 | 10/1970 | Gittos et al. | 564/428 |
| 3,758,690 | 9/1973 | Gittos et al. | 514/657 |
| 3,930,022 | 12/1975 | Houck et al. | 564/374 X |
| 4,181,738 | 1/1980 | Ginos et al. | 564/374 X |
| 4,314,082 | 2/1982 | Stout | 564/381 |

OTHER PUBLICATIONS

Stout (II), "Jour. Med. Chem.", vol. 25, pp. 326–328 (1982).
Dren et al., "Chemical Abstracts", vol. 89, pp. 77–78, Section No. 1000065f (1978).
Gorczynski et al., "Journal of Medicinal Chemistry", vol. 24, No. 7, pp. 835–839 (1981).
McDermed, J., et al. J. Med. Chem. 18(4): 362–367 (1975).
Hall, A. W. et al. J. Med. Chem. 30: 1897–1887 (1987).

*Primary Examiner*—Richard L. Raymond
*Attorney, Agent, or Firm*—Ladas & Parry

[57] ABSTRACT

N-alkyl derivatives of 2-amino-6,7-dimethoxy tetraline having general formula (I)

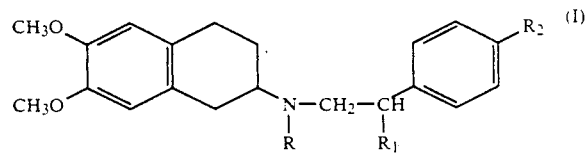

wherein
R is selected from hydrogen, ethyl, n-propyl and methyl cyclopropyl;
$R_1$ is selected from hydrogen, hydroxy and $-OR_3$ wherein $R_3$ is selected from methyl, ethyl and n-propyl; and
$R_2$ is selected from hydrogen, methyl, hydroxy, trifluoromethyl, fluoro and methoxy, are endowed with potent antihypertensive activity.

20 Claims, No Drawings

N-ALKYL DERIVATIVES OF 2-AMINO-6,7-DIMETHOXY TETRALINE AND PHARMACEUTICAL COMPOSITIONS HAVING ANTIHYPERTENSIVE ACTIVITY CONTAINING SAME

The present invention relates to N-alkyl derivatives of 2-amino-6,7-dimethoxy tetraline having general formula (I);

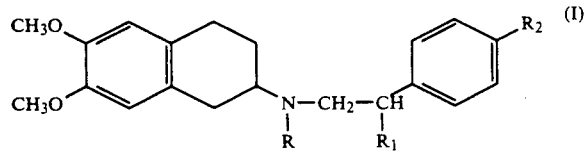

wherein
R is selected from hydrogen, ethyl, n-propyl and methyl cyclopropyl;
$R_1$ is selected from hydrogen, hydroxy and $-OR_3$ wherein $R_3$ is selected from methyl, ethyl and n-propyl; and
$R_2$ is selected from hydrogen, methyl, hydroxy, trifluoromethyl, fluoro and methoxy.

The compounds of general formula (I) are endowed with potent antihypertensive activity.

The present invention also relates to the processes for producing the compounds of general formula (I) and to the pharmaceutical compositions which comprise a compound of general formula (I) as active principle.

Tetraline derivatives loosely related to the compounds of the present invention from a structural viewpoint are disclosed in the UK patent 1,377,356 and in the European patent application 64964. However, in addition to being different in structure, the known tetraline derivatives possess pharmacological activities totally different from and unrelated to the antihypertensive activity shown by the compounds of general formula (I).

In fact, the compounds of the British patent exhibit analgesic activity, while the compounds disclosed and claimed in the European patent application are active on the central nervous system and can be used for the therapeutical treatment of psychopathias such as schizophrenia.

In general, the compounds of formula (I) are prepared by condensing 2-amino-6,7-dimethoxy tetraline (wherein the amino group is optionally substituted with ethyl, n-propyl or methylcyclopropyl, having regard to the specific compound (I) which one wants to obtain) with an activated form of phenylacetic acid or mandelic acid of formula

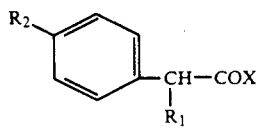

wherein
$R_1$ and $R_2$ have the previously defined meanings; and
X is either Cl or the

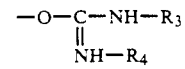

residue wherein $R_3$ and $R_4$ are either alkyl radicals having from 1 to 3 carbon atoms or cyclopropyl radicals having 5 or 6 carbon atoms.

The condensation is carried out in an inert anhydrous organic solvent, such as ethyl acetate or methylene chloride.

Preferably the aminotetraline/acid ratio is about 2:1. The reaction temperature is comprised between about 0° C. and 25° C.

The amide thus obtained is reduced with borohydride in an inert solvent, e.g. tetrahydrofurane, in an atmosphere of inert gas, at a temperature comprised between about 0° C. and 10° C.

The amide/borohydride ratio is comprised between about 1:3.5 and 1:2.5. The compound is isolated as hydrochloride.

EXAMPLE 1

Preparation of 2-[(N-methylcyclopropyl, N-p-methoxy-phenyl-2-ethanol)amino]-6,7-dimethoxy tetraline hydrochloride (ST 565).

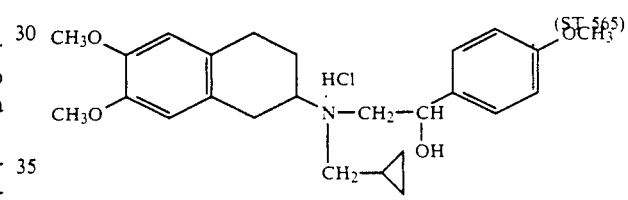

(a) Preparation of 2-(N-methylcyclopropyl)amino-6,7-dimethoxy tetraline hydrochloride (ST 544).

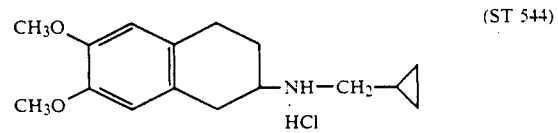

2-amino-6,7-dimethoxy tetraline (11 g; 0.053 moles) was dissolved in 100 ml of acetone and placed in a two-necked round-bottom flask equipped with a loading funnel with 2.4 ml of the acid chloride of cyclopropanecarboxylic acid (0.0265 moles). The acid chloride was added to the solution very slowly at room temperature. After 30 minutes the solution was filtered. The filtrate was washed with AcOEt in order to be used again. The organic phase was brought to dryness and taken up with methylene chloride, washed, first with a 1N NaOH solution, then with 1N HCl and then with $H_2O$ to neutrality, dried over anhydrous $Na_2SO_4$ and brought to dryness. The white solid thus obtained (7.2 g; yield 98%) was placed in a three-necked round-bottom flask equipped with a cooler and dehydrated under a nitrogen stream.

The temperature was brought to 0° C. and 91.6 ml (0.0916 moles) of a 1M $BH_3$ solution in tetrahydrofurane (THF) were added (substrate: $BH_3$ molar ratio 1:3.5).

The solution was kept at its reflux temperature for 3 hours, then the temperature was brought again to 0° C., 80 ml of 6NHCl were added.

The solution was kept again at the reflux temperature for 30 minutes, then THF was removed under vacuum.

The resulting acid aqueous solution was washed with AcOEt, alkalinized with 4N NaOH to a distinct basic pH and extracted with methylene chloride.

The organic phase was washed with H₂O to neutrality and dried over anhydrous Na₂SO₄. The residue was dissolved with AcOEt, and gaseous HCl was bubbled in the resulting solution while keeping the temperature at 0° C.

Crystalline ST 544 precipitated which was filtered off. 6.28 g of the compound (yield 92%) were obtained.

Elementary analysis: corresponding to $C_{16}H_{24}ClNO_2$.

NMR D₂O δ0.6 (4H, m,

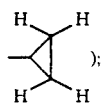
);

1.1 (1H, m,

);

1.9 (2H, m,

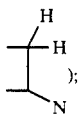
);

2-3 (6H, m,

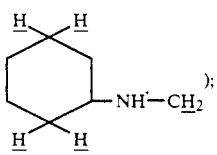
);

3.8 (6H, s,

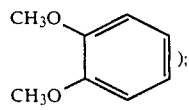
);

6.8 (2H,s,

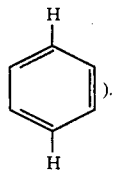
).

P.F.=245°-246° C.

(b) Condensation and Reduction 2-(N-methyl cyclopropyl)amino-6,7-dimethoxy tetraline (3.5 g; 0.013 moles) was dissolved in 10 ml of acetone. To the resulting solution cooled to 0° C. the acid chloride of O-acetyl para-methoxy mandelic acid (1.9 g; 0.008 moles) was added. The solution was kept under stirring for 30 minutes and then brought to dryness. The residue was dissolved in AcOEt, the solution was filtered and washed with 1N HCl, 1N NaOH and H₂O to neutrality. The solution was concentrated under vacuum and 3 grams of a raw product were obtained (yield 95%).

To the amide thus obtained 40 ml of 1M BH₃ in THF were added and the resulting solution was kept at the reflux temperature for 3 hours. Subsequently, 50 ml of 6N HCl were added at 0° C. The solution was kept at the reflux temperature for 15 minutes and then concentrated under vacuum to remove the THF. The acid solution was washed with AcOEt, brought to basic pH with 4N NaOH and extracted with methylene chloride. The organic phase was washed with H₂O to neutrality and brought to dryness. The residue was chromatographed over silica gel with AcOEt/MeOH 9:1 as eluent. 280 mg of product were obtained.

Elementary analysis: corresponding to $C_{25}H_{34}ClNO_4$.

NMR, CDCl₃ δ7÷6.5 (4H,m,arom.); 6.5 (2H,m,arom.tetraline); 4.6 (1H,t,

);

3.8 (6H,s,(OCH₃)₂); 3.75 (3H,s,OCH₃); 3.2+2.6 (9H,m,

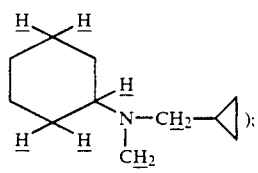
);

2.2-1.5 (3H,m,

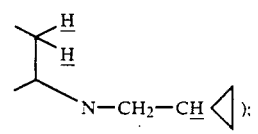
);

1.5÷0.5 (4H

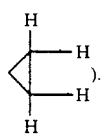
).

EXAMPLE 2

Preparation of
2-[(N-propyl,N-phenyl-2-ethanol)amino]-6,7-dimethoxy tetraline hydrochloride (ST 566)

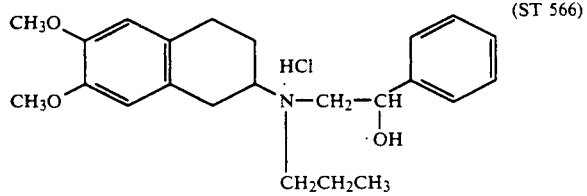

(a) Preparation of 2-(N-propyl)amino-6,7-dimethoxy tetraline hydrochloride

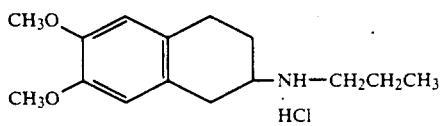

2-amino-6,7-dimethoxytetraline (3.3 g; 0.016 moles) was dissolved in 59 cc of ethyl acetate, and propionyl chloride (0.7 cc; 0.008 moles) was added at 0° C. to the solution. The solution was then kept at the room temperature under stirring for 1 hour.

Subsequently, the solution was filtered and washed with 5% HCl, then with 5% NaHCO₃ and finally with H₂O to neutrality. The solution was then dried over anhydrous Na₂SO₄ and concentrated under vacuum. 1.2 g of 2-N-propionylamino-6,7-dimethoxy tetraline were obtained as a solid product. This product was dissolved in 15 cc of anhydrous THF and the solution was added to the solution of BH₃ in THF (19 cc; 0.019 moles) at 0° C. After the solution was kept at the reflux temperature for three hours and then cooled to 0° C., 10 cc of 6N HCl were added. The resulting solution was again kept at the reflux temperature for 30 minutes and then concentrated under vacuum in order to remove the THF. The acid aqueous solution was alkalinized with 4N NaOH to a distinctly alkaline pH and extracted with methylene chloride. The solution of methylene chloride was washed with H₂O to neutrality, dried over Na₂SO₄ and concentrated to dryness. The resulting oily residue was dissolved in 6N HCl and concentrated under vacuum giving 1 g of a solid product.

NMR D₂O $\delta$6.7 (2H, m, arom): 3.8 (6H, s,(OCH₃)₂); 3÷2.5 (7H, m

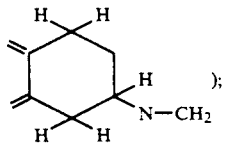

2.2–1.4 (4H, m,

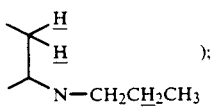

1.0 (3H, t, —CH₂C$\underline{H}$₃).

(b) Condensation and Reduction 2-(N-propyl)amino-6,7-dimethoxy tetraline (4.5 g; 0.0178 moles) was dissolved in 50 ml of acetone. The solution was filtered at 0° C. and the acid chloride of O-acetyl mandelic acid (2.0 ml; 0.0089 moles) was added dropwise. The resulting solution was kept at room temperature for 30 minutes. The filtered solution was concentrated under vacuum, the residue was taken up with ethylene chloride and washed with 1N HCl, 1N NaOH and H₂O to neutrality. The organic phase was dried over anhydrous Na₂SO₄ and brought to dryness. 2.5 g (yield 72%) of 2-[(N-propyl,N-mandelyl O-acetyl)amino]-6,7-dimethoxy tetraline were obtained. To the amide thus obtained 33 moles of a solution of BH₃ in TFH were added at 0° C. and the resulting mixture was kept at the reflux temperature under a nitrogen stream for three hours. Subsequently, 33 ml of 6N HCl were added at 0° C. and the resulting solution was kept at the reflux temperature for 30 minutes and then concentrated under vacuum in order to remove the THF. The remaining acid solution was washed with AcOEt and then alkalinized with 4N NaOH and extracted with methylene chloride. The phase containing the methylene chloride was washed with H₂O to neutrality and concentrated under vacuum. The solid which was obtained was taken up with AcOEt, gaseous HCl was bubbled in the solution thus giving a white solid product (1.7 g; yield=74%).

TLC (AcOEt MeOH NH₄OH 9:9:0.5) R$_F$ 0.7.

Elementary analysis corresponding to C₂₃H₃₂ClNO₃.

NMR CDCl₃ $\delta$7.3 (5H, m; arom.); 6.5 (2H,m;arom.-tetraline). 3.8 (6H, s,

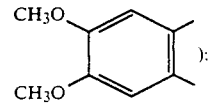

2.9÷2.4 (10H, m,

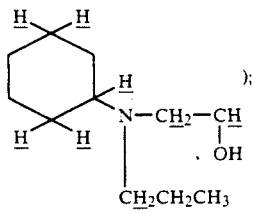

2.0÷1.0 (4H, m,

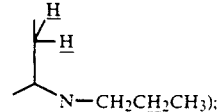

0.8 (3H, t, CH₂—C$\underline{H}$₃).

EXAMPLE 3

Preparation of 2-[(N-methyl cyclopropyl, N-phenyl-2-ethanol)amino]-6,7-dimethoxy tetraline hydrochloride (ST 567)

(ST 567)

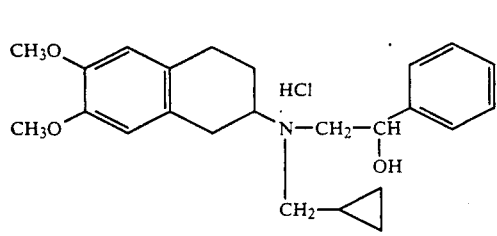

2-(N-methyl cyclopropyl)amino-6,7-dimethoxy amino tetraline (2 g; 0.0089 moles) (prepared as indicated in step (a) of Example 1) was dissolved in ethyl acetate and to the resulting solution the acid chloride of O-acetyl mandelic acid (1 ml; 0.0044 moles) was added at 0° C. A precipitate formed which was filtered off and the filtrate was washed first with 1N NaOH, then with 1N HCl and finally with $H_2O$. The organic phase was dried over anhydrous $Na_2SO_4$ and concentrated.

1.5 g of 2-[N-methyl cyclopropyl, N-mandelyl O-acetyl)amino]-6,7-dimethoxy tetraline were obtained.

To this solid, placed in a round-bottom flask equipped with a cooler, 17 ml of a 1M $BH_3$ solution in THF were added under a nitrogen stream, and the resulting solution was kept at the reflux temperature for three hours. Subsequently, 30 ml of 6N HCl were added at 0° C. and the solution was again kept at the reflux temperature for 30 minutes. Then, THF was removed under vacuum. The remaining acid solution was shaken with methylene chloride. The resulting organic phase was washed with $H_2O$ to neutrality, dried over anhydrous $Na_2SO_4$ and brought to dryness. The solid thus obtained was dissolved in acetyl acetate and gaseous HCl was bubbled therein. The solid which formed was filtered off: 1.03 g of the title product were obtained (yield 70%).

Elementary analysis: corresponding to $C_{24}H_{32}ClNO_3$.

NMR CDCl$_3$ δ7.3 (5H,m,arom.); 6.5 (2H,m,arom.tetraline); 3.8 (6H, s, $(OCH_3)_2$); 3.5-2.5 (10H, m,

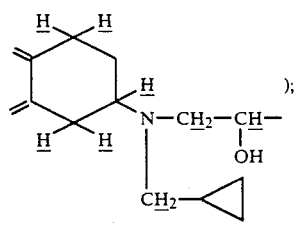

);

2.4-0.5 (7H, m,

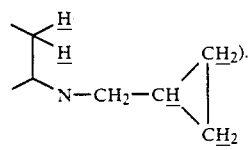

EXAMPLE 4

Preparation of 2-[(N-propyl,N-2-p-methyl phenyl-2-ethanol)amino]-6,7-dimethoxy tetraline hydrochloride (ST 571)

(ST 571)

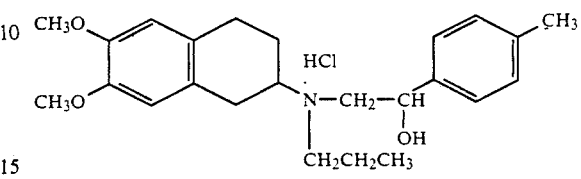

2-(N-propyl)amino-6,7-dimethoxy tetraline (3.69 g; 0.0147 moles) (prepared as indicated in step (a) of Example 2 was dissolved in 43 cc of acetone. To the resulting solution the acid chloride of p-methyl-O-acetyl-mandelic acid (1.45 g; 0.007 moles) was added. The solution was kept at room temperature for 30 minutes and subsequently filtered and concentrated under vacuum. The residue was taken up with methylene chloride and washed with 5% HCl, 5% NaHCO$_3$ and $H_2O$ to neutrality. The organic phase was dried over anhydrous $Na_2SO_4$ and brought to dryness. 2.4 g of 2-[(N-propyl, N-p-methyl-O-acetyl mandelyl)amino]-6,7-dimethoxy tetraline were obtained. To the amide thus obtained (2.4 g; 0.0058 moles) BH$_3$ in THF (17.4 cc; 0.017 moles) was added at 0° C. The solution was kept at the reflux temperature for three hours. Subsequently, 16 cc of 6N HCl were added at 0° C., the solution was kept at the reflux temperature for 30 minutes and then concentrated under vacuum in order to remove the THF. The acid solution was alkalinized with 4N NaOH and extracted with chlorphorm. The organic phase was washed with $H_2O$ to neutrality and concentrated under vacuum. The solid which formed was taken up with ethyl acetate and upon addition of gaseous HCl 1.4 grams of a white solid product were obtained (yield 74%).

TLC AcOEt, MetOH, NH$_4$OH R$_F$ 0.8
        9     1      0.5

NMR CDCl$_3$ δ7.1 (4H, m,

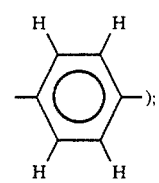

);

6.5 (2H,m,

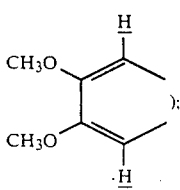

);

3.6 (6H, s, $(O—CH_3)_2$); 3.6-2.5 (10H,m,

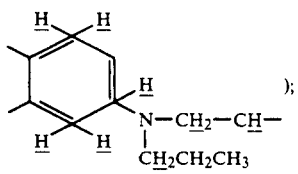

2.1 (3H,s,

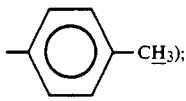

2–0.8 (7H,

—CH₂CH₃).

Elementary analysis corresponding to $C_{24}H_{33}ClNO_3$.

EXAMPLE 5

Preparation of
2-[(N-2-phenyl-2-ethanol)amino]-6,7-dimethoxy
tetraline hydrochloride (ST 579)

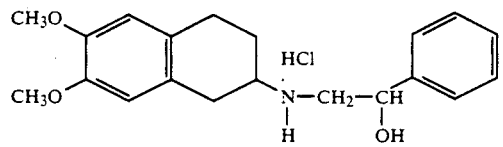

(ST 579)

The compound was prepared as described in Example 2, using as starting material 2-amino-6,7-dimethoxy tetraline. Yield 76%.

Elementary analysis: corresponding to $C_{20}H_{25}ClNO_3$.

Melting point: 212°–215° C.

NMR DMSO δ7.5 (5H, s, aromatic); 6.5 (2H,s

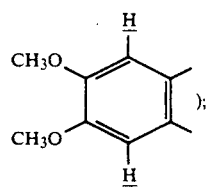

4.5 (1H, m,

3.8 (6H, s,

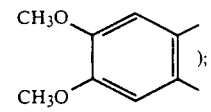

3.5–1.5 (9H, m,

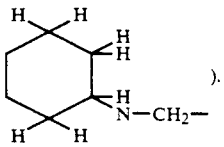

EXAMPLE 6

Preparation of 2-[(N-ethyl, N-2-phenyl ethyl)amino]-6,7-dimethoxy tetraline hydrochloride (ST 577)

(ST 577)

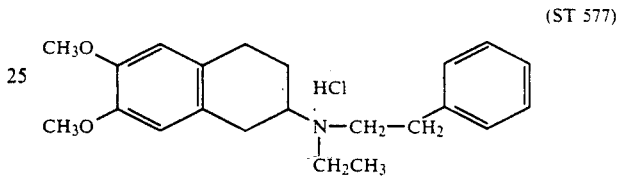

The compound was prepared as described in Example 2, using as starting materials the acid chloride of the phenyl acetic acid and 2-(N-ethyl)amino-6,7-dimethoxy tetraline which was prepared as hereinbelow indicated.

In a three-necked round bottom flask equipped with a cooler and kept under a nitrogen stream, 3 g (0.012 moles) of N-acetyl amino-6,7-dimethoxy tetraline were placed; 30 ml of a 1M solution of $BH_3$ in THF (0.030 moles) were added at a temperature comprised between 0° C. and 4° C. The resulting solution was kept at the reflux temperature for three hours, then the temperature was again brought to 0° C. -4° C. 32 ml of 6N HCl were then added dropwise. The solution was again kept at the reflux temperature for 30 minutes, then the THF was removed under vacuum. The acid aqueous solution was washed with ethyl acetate, alkalinized with NaOH to a distinctly basic pH and extracted with methylene chloride. The organic phase was washed with $H_2O$ to neutrality, dried over anhydrous $Na_2SO_4$ and concentrated under vacuum. The residue was dissolved in ethyl acetate, gaseous HCl was bubbled in the solution while keeping the temperature at 0° C. 2-(N-ethyl)amino-6,7-dimethoxy tetraline hydrochloride precipitated as a solid product which was filtered off. 2.9 g (yield 90%) were obtained.

Melting Point: 230° C.

Elementary analysis: corresponding to $C_{14}H_{23}ClNO_2$.

NMR $D_2O$ δ6.7 (2H, m, arom.); 3.8 (6H,s, (OCH₃)₂); 3.2 (2H,q, N—CH₂—CH₃); 3.2÷2.6 (5H,m,

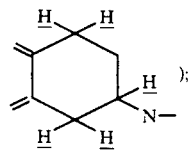

2÷1.8 (2H, m,

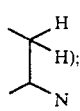

1.4 (3H, t, NCH₂CH₃).

The title compound (ST 577) was obtained (yield 55%).

Elementary analysis: corresponding to C₂₂H₄₀ClNO₂.

NMR CDCl₃ δ7.5 (5H, s, aromatic); 6.5 (2H, s

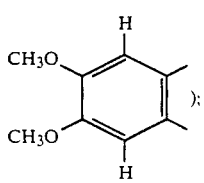

3.8 (6H, s,

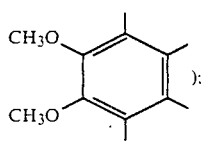

3.5–1.8 (13H, m,

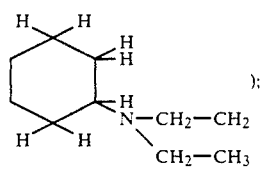

1.4(3H,t, N—CH₂CH₃).

EXAMPLE 7

Preparation of 2-[(N-methyl cyclopropyl, N-p-methyl phenyl-2-ethanol)amino]-6,7-dimethoxy tetraline hydrochloride (ST 574).

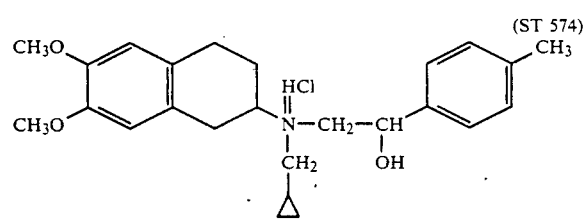

The compound was prepared as described in Example 3, using the acid chloride of p-methyl O-acetyl mandelic acid as starting material in lieu of the acid chloride of the O-acethyl mandelic acid.

Elementary analysis: corresponding to C₂₅H₃₄ClNO₃.

Melting point 130° C. -135° C.

NMR CDCl₃ δ7.2 (4H, m, aromatic); 6.5 (2H, m

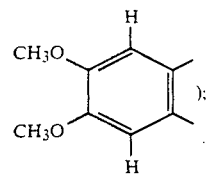

4.0 (1H, m,

3.8 (6H, s,

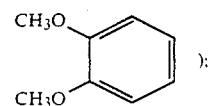

3.6–1.0 (16H, m,

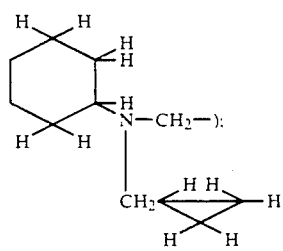

2.3 (3H, s,

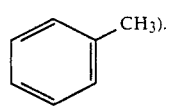

EXAMPLE 8

Preparation of 2-[(N-ethyl, N-2-methyl phenyl-2-ethanol)amino]-6,7-dimethoxy tetraline hydrochloride (ST 587)

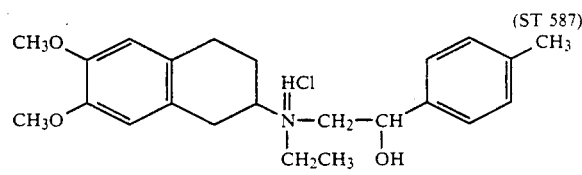

The compound was prepared as described in Example 4 using as starting material 2-(N-ethyl)amino-6,7-dimethoxy tetraline prepared as indicated in Example 6.

Yield 25%.

Elementary analysis: corresponding to C₂₃H₃₂ClNO₃.

Melting point 125°–130° C.

NMR CDCl₃ δ7.2 (4H, m; aromatic); 6.5 (2H.m, 4,6 (1H, m, 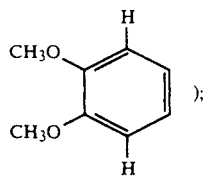);

—CH—);
|
OH 3.8 (6H, s, 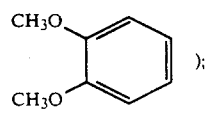);

3.5-2 (9H,m, 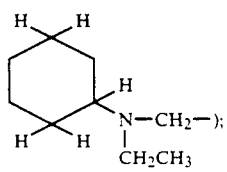);

2,3 (3H, s, 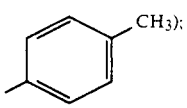);

2-0.5 (5H,m, —CH$_2$CH$_3$, 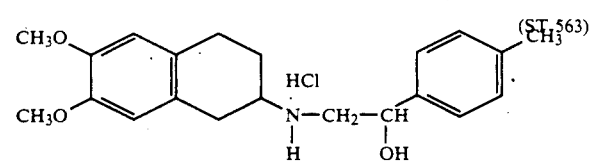).

EXAMPLE 9

Preparation of 2-[(N-2-p-methyl phenyl-2-ethanol)amino]-6,7-dimethoxy tetraline (ST 563)

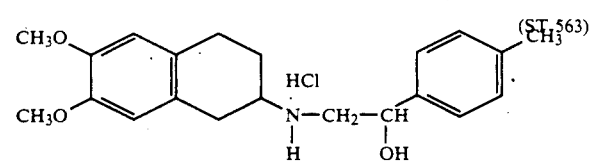

The compound was prepared as described in Example 4, using as starting material 2-amino 6,7-dimethoxy tetraline.
Yield 63%.
Elementary analysis: corresponding to C$_{21}$H$_{28}$ClNO$_3$.
Melting point 195°-200° C.
NMR CDCl$_3$ δ7.0 (4H, m, aromatic); 6.2 (2H, m 4.5 (1H, m, 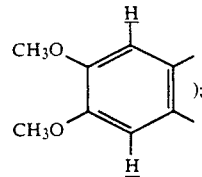);

—CH—);
|
OH 3.8 (6H,s, 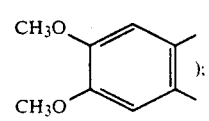);

3.2-1.5 (9H, m, 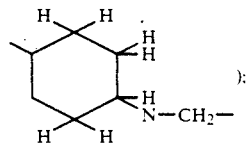);

2.3 (3H,s, 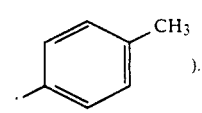).

EXAMPLE 10

Preparation of 2-[(N-ethyl, N-2-phenyl-2-ethanol)amino]-6,7-dimethoxy tetraline hydrochloride (ST 570

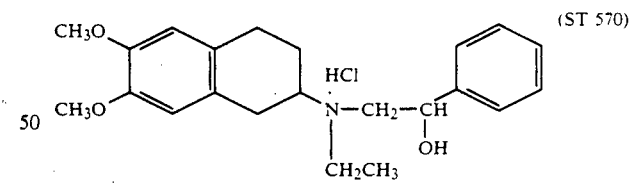

The compound was prepared as described in Example 2 using as starting material 2-(N-ethyl) amino-6,7-dimethoxy tetraline.
Yield 76%.
Elementary analysis corresponding to C$_{22}$H$_{30}$ClNO$_3$.
NMR CDCl$_3$ δ7.3(5H,m; aromatic); 6.5 (2H,m, 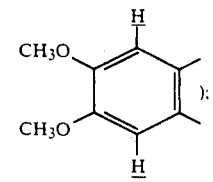);

5.1 (1H, m,

—CH—);
  |
  OH 3.8 (6H, s,

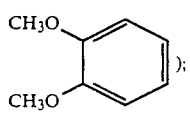
);

3.5–1.0 (14H, m,

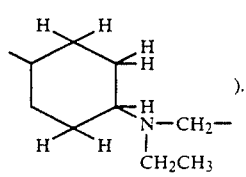
).

EXAMPLE 11

Preparation of 2-[(N-2-p-methoxyphenyl-2-ethanol)amino]-6,7-dimethoxy tetraline hydrochloride (ST 578)

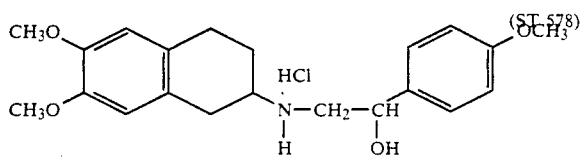

The compound as prepared as described in Example 1 using as starting material 2-amino-6,7-dimethoxy tetraline.

Elementary analysis: corresponding to $C_{21}H_{28}ClNO_4$.

NMR CDCl$_3$ δ7.2–7.0 (4H,m; aromatic); 6.5 (2H,m,

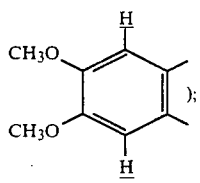
);

4.7 (1H, m,

—CH—);
  |
  OH 3.8 (6H, s,

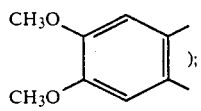
);

3.7 (3H,s,

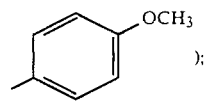
);

3.2–2.5 (7H,m,

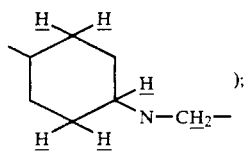
);

2.5–1.8 (2H,m,

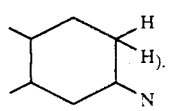

EXAMPLE 12

Preparation of 2-[(N-2-phenyl-2-methoxy ethyl) amino]-6,7-dimethoxy tetraline hydrochloride (ST 600)

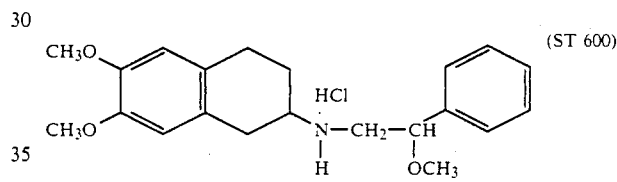

To a solution of methoxy mandelic acid (2.04 g; 0.012 moles) in acetonitrile (10 ml), dicyclohexylcarbodiimide (2.88 g; 0.014 moles) was added at 0° C. The solution was kept under stirring for 40 minutes and subsequently a solution of 2-amino-6,7-dimethoxy tetraline (2.55 g; 0.12 moles) in 10 ml of acetonitrile was added dropwise. The resulting mixture was kept at room temperature for 1 hour under stirring. The solid which formed was removed, the solution was diluted with methylene chloride and washed with 5% HCl, a saturated solution of NaHCO$_3$ and finally with H$_2$O to neutrality. The organic phase which separated was dried over anhydrous Na$_2$SO$_4$ and concentrated furnishing a gelatinous residue of 4.8 g to which 45.4 ml (0.046 moles) of BH$_3$ of THF were added. The solution was kept at the reflux temperature for 2 hours and cooled to 0° C. 40 ml of 4N HCl were added to the solution which was then kept at the reflux temperature for 1 hour. The solution was then concentrated under vacuum in order to remove THF, its pH was adjusted to a basic value with 4N NaOH, and repeatedly extracted with methylene chloride. The organic phase was washed with H$_2$O, dried over anhydrous Na$_2$SO$_4$ and concetrated to dryness. The residue was taken up with ethyl acetate and gaseous HCl was bubbled in the solution thus obtained. 3.3 g of a white solid were obtained. Yield 69%.

Elementary analysis: corresponding to $C_{21}H_{28}ClNO_3$.

Melting point 198° C.–201° C.

NMR CDCl$_3$ δ7.3 (5H,m, aromatic); 6.5 (2H,m,

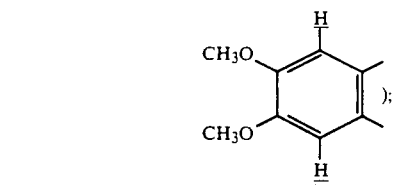

4.9 (1H, m,

3.8 (6H, s,

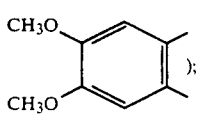

3.3 (3H, s,

3.0–1.0 (9H, m,

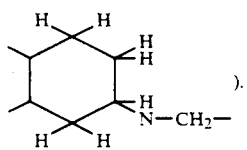

).

EXAMPLE 13

Preparation of 2-[(N-2-p-trifluoromethylphenyl-2-ethanol)amino]6,7-dimethoxy tetraline hydrochloride (ST 590)

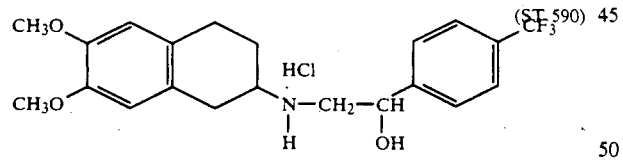

The compound was prepared as described in Example 12 using as starting material p-trifluoromethyl mandelic acid. Yield 30%.

Elementary analysis: corresponding $C_{21}H_{25}ClF_3NO_3$.

Melting point 201°–203° C.

NMR CDCl$_3$ δ7.7(4H,m,aromatic); 6.4 (2H,m,

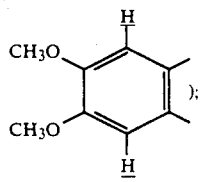

4.2 (1H, m,

3.8 (6H, s,

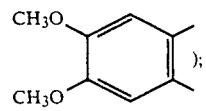

3.5–1.8 (9H, m,

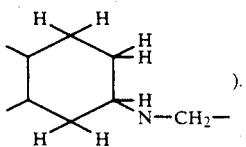

).

EXAMPLE 14

Preparation of 2-[(N-ethyl, N-2-p-trifluoro methyl phenyl-2-ethanol)-amino]-6,7-dimethoxy tetraline hydrochloride (ST 592)

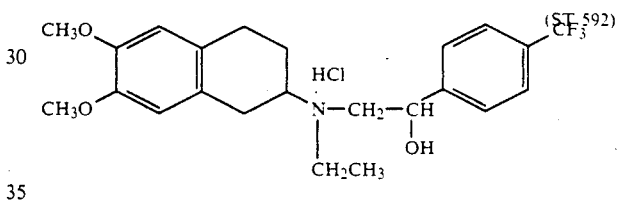

The compound was prepared as described in Example 13, using as starting material 2-(N-ethyl)amino 6,7-dimethoxy tetraline.

Yield 30%.

Elementary analysis: corresponding to $C_{23}H_{29}ClF_3NO_3$.

Melting point 178°–180° C.

NMR CDCl$_3$ δ8.1–7.5 (4H, m, aromatic); 6.5 (2H,m,

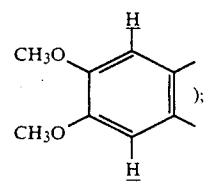

4.3 (1H, m,

3.8 (6H, s,

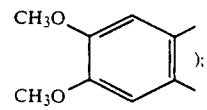

3.6–1.8 (11H, m,

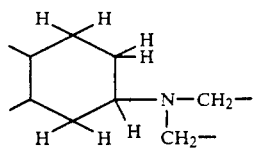

1.5 (3H, t, N—CH$_2$—C$\underline{H}_3$).

EXAMPLE 15

Preparation of 2-[(N-2-p-fluoro phenyl-2-ethanol)amino]-6,7-dimethoxy tetraline hydrochloride (ST 593)

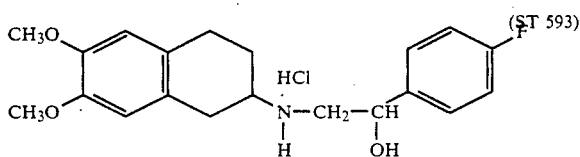

THe compound was prepared as described in Example 12 using as starting material p-fluoro mandelic acid.
Yield 30.
Elementary analysis: corresponding to C$_{20}$H$_{25}$ClFNO$_3$.
Melting point 93°–95° C.
NMR CDCl$_3$ δ7.5–6.8 (4H,m,aromatic); 6.5 (2H,m,

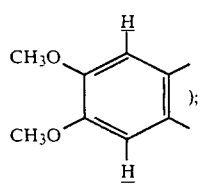

5.5 (1H, m,
3.8 (6H, s,

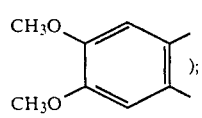

3.6–1.8 (9H, m,

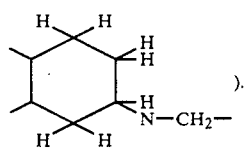

EXAMPLE 16

Preparation of 2-[(N-2-p-hydroxyphenyl-2-ethanol)amino]-6,7-dimethoxy tetraline hydrochloride (ST 558)

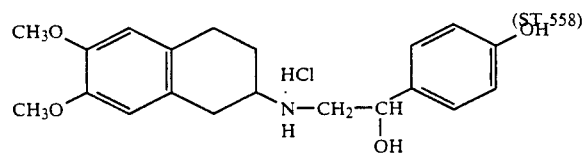

(a) Preparation of p-benziloxy Mandelic Acid 4-benziloxy benzaldehyde (21.2 g; 0.1 moles) was dissolved in 16 ml of CHCl$_3$. To the solution, 1.14 g of triethyl benzylammonium chloride and 25 ml of 50% NaOH were added. The reaction mixture was kept at 60° C. for 1 hour. The phases were separated.

The aqueous phase was washed with ethyl ether, acidified with 50% H$_2$SO$_4$ and repeadetly extracted with ethyl ether. The organic phase, after being washed with H$_2$O, was concentrated under vacuum, 11.6 g of the title product were obtained, which were crystallized from toluene.

(b) Preparation of 2-[(N-2-p-benziloxy phenyl-2-ethanol)amino]-6,7-dimethoxy tetraline p-benziloxy mandelic acid was acetylated according to known procedures and the acetylation product was condensed with 6,7-dimethoxy amino tetraline according to "acid chloride method", as described in example 2. The overall yield of the title product was 22%.

(c) Preparation of ST 558

2.5 g of the compounds of step (b) were dissolved in 30 ml of absolute ethanol and 6 ml of ethyl acetate. The resulting solution was hydrogenated for 1 hour at 3 atmospheres, at room temperature, using 10% Pd/C as catalyst. The solution was filtered and concentrated under vacuum, the residue was dissolved in ethyl acetate and gaseous HCl was bubbled in the solution. 1.54 g of a white precipitate were obtained (Yield 71%).
Elementary analysis: corresponding to C$_{20}$H$_{25}$ClNO$_4$.
NMR CDCl$_3$-DMSO δ7.3–6.6(4H,q.aromatic); 6.5(2H,s

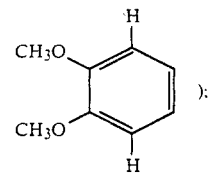

4.6 (1H, t,

3.8 (6H, s, (OCH$_3$)$_2$); 3.2 (1H, m,

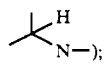

3.0–2.0 (8H, m,

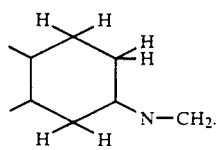

The low toxicity and the potent antihypertensive activity of the compounds of the present invention were assessed via several tests. The methods employed and the results of some of these tests are illustrated hereinbelow.

TOXICOLOGICAL TESTS

(a) Tolerability

Male Albino Swiss mice weighing 22-24 g were used in this test.

One group of animals (4/does) which had been kept fasting for 18 hours was orally administered the compounds dissolved in twice distilled water. The same compounds dissolved in saline at pH-7 were intravenously injected in a further group of animals which had free access to food and drinking water. All of the animals were monitored for 7 days.

The test results are reported in the first column of table 1.

(b) LD50

LD50 was assessed according to the Carrol S. Weil's method (Biometrics, pages 249-263 (1952)) on male Albino Swiss mice weighing 22-24 g. The compounds dissolved in 9% saline solution were administered via the intravenous route. The results are illustrated in table 2.

TABLE 2

| Compound | LD50 mg/kg | from mg/kg | to mg/kg |
| --- | --- | --- | --- |
| ST 579 | 35.71 | 43.37 | 29.41 |

TABLE 2-continued

| Compound | LD50 mg/kg | from mg/kg | to mg/kg |
| --- | --- | --- | --- |
| ST 570 | 34.92 | 44.30 | 27.53 |
| ST 567 | 30.18 | 39.71 | 22.93 |
| ST 563 | 35.71 | 43.37 | 29.41 |
| ST 589 | 35.71 | 43.37 | 29.41 |
| ST 571 | 42.26 | 42.26 | 42.26 |
| ST 578 | 27.74 | 32.82 | 23.44 |
| ST 577 | 35.71 | 43.37 | 29.41 |
| ST 600 | 29.68 | 29.68 | 29.68 |

PHARMACOLOGICAL TESTS

(a) Measure of Arterial Pressure in Cats

Normotensive cats of either sex weighing 2.5-3.5 kgs were used in this test.

The animals fasted for 18 hours were anesthetized with Na Nembutal (30 mg/kg) and ethyl urethane (300 mg/kg i.p.). The crural vein and artery of the animals were cannulated, the former for administering the compounds, the latter for monitoring the arterial pressure. The arterial pressure was measured via a mercury gauge connected to a rotating kymograph.

The compounds were dissolved in sterile 0.9% saline and administered at physiological pH in a 0.5 ml/kg volume.

The results are illustrated in the second column of table 1.

TABLE 1

| COMPOUNDS | I TOLERABILITY dose mg/kg os | I TOLERABILITY dose mg/kg i.v. | II ARTERIAL PRESSURE IN NORMOTENSIVE CATS dose mg/kg hypotension mm Hg | III ARTERIAL PRESSURE IN HYPERTENSIVE SHR RATS dose mg/kg mm Hg | IV ARTERIAL PRESSURE IN HYPERTENSIVE DOCA RATS dose mg/kg mm Hg |
| --- | --- | --- | --- | --- | --- |
| ST 579 | >50 | >20 | 1-2-4 mg 18-50 L | 40 mg −26 (2 hours) | 40 mg −20 (2-4 hours) |
| ST 570 | >50 | >20 | 1 mg 64 L | 40 mg −29 (2 hours) | |
| ST 566 | >50 | >20 | 0.01-1 mg 12-72 B | | |
| ST 567 | >50 | >15 | 1-4 mg 0-16 B | −15 (2 hours) | |
| ST 563 | >50 | >20 | 1-2-4 mg 18-46 L | 40 mg −65 (2 hours) | 40 mg −20/−30 (4-6 hours) |
| ST 587 | >50 | >20 | 1 mg 30 L | | |
| ST 571 | >50 | >30 | 1-2-4 mg 12-30 M/B | 20-40 mg 0 | |
| ST 574 | >50 | >30 | 1-2-4 mg 12-30 M/B | 20-40 mg 0 | |
| ST 578 | >50 | >15 | 1-2-4 mg 16-30 B/L | 40 mg −40 (3 hours) −27 (5 hours) | |
| ST 565 | >50 | | 0.5-1 mg 20-30 B | | |
| ST 558 | >50 | >50 | 1-4 mg 10-14 L | 40 mg −13 (3 hours) −31 (5 hours) | |
| ST 590 | >50 | >50 | 40 mg (os) (1) 39 L (2) 0 | | |
| ST 592 | >50 | >30 | 1-2-4 mg 0 | | |
| ST 593 | >50 | >50 | 1-2-4 mg 12-16-26 M/B | | |
| ST 577 | >50 | >20 | 1 mg 20 L 2 mg 44 M | 10-20 mg 0 | |
| ST 600 | >50 | >20 | 2 mg 28 B 4 mg 54 M | | |

Times of effect duration
B = short <5 minutes
M = average ≦30 minutes
L = long >30 minutes (b) Non-invasive Measure of Arterial Pressure in Genetically Hypertensive Rats Male SHR rats (Charles River) of 4-6 months were used in this test. The compounds listed were dissolved in either 0.9% saline or twice distilled water and administered via the oral route (10-40 mg/5 ml/kg).

The animals, housed in individual cages at 23° C. and 60% humidity, had free access to food and drinking water. A BP recorder (Letica) equipped with a two-way polygraph was used. The systolic and diastolic pressure and the heart rate were recorded. The animals, a few days before the test began, were accustomed to be constrained on a heating plate (at 38° C.±1° C. for 20 minutes).

During the pre-tests, assessments were made at time 0 ($8^{30}$-$9^{30}$ a.m.) and after 2 and 4 hours.

Every assessment was the average of 3-5 measures and the maximum residence time of the animal in the thermostatized chamber (for the whole test duration) was 40 minutes; the time interval between administrations of different doses of the same compound was 3 days.

Student's "t" test was used for assessing the differences with respect to the control group and its own 0 time.

The results are shown in the third column of table 1.

(c) Non-invasive Measure of the Arterial Pressure in Rats Made Hypertensive

Male Wistar rats (Charles River) of 4 months were used in this test.

The compounds listed were solubilized in twice distilled water and administered via the oral route (40 mg/5 ml/kg).

The animals, housed in individual cages at 23° C. and 60% humidity, had free access to food and were made to drink 1% saline solution. The animals were administered 20 mg/kg s.c. of deoxycorticosterone acetate (DOCA) for 14 days on end.

A BP recorder (Letica) equipped with a two-way polygraph was used. The systolic and diastolic pressure, and the heart rate were recorded. The animals, a few days before the test began, were accustomed to be constrained on a heating plate (at 38° C.±1° C. for 20 minutes).

During the pre-test, assessments were made at time 0 ($8^{30}$-$9^{30}$ a.m.) and after 2 and 4 hours.

Every assessment was the average of 3-5 measures and the maximum residence time of animal in the thermostatized chamber (for the whole test duration) was 40 minutes; the time interval between administrations of different doses of the same compound was 3 days.

Student's "t" test was used for assessing the differences with respect to the control group and its own 0 time.

The results are shown in the third column of table 1.

The dose of the compounds of formula (I) to be administered will be determined having regard to the age, weight and general conditions of the patient. Effective results can be obtained with dose of about 0.5-5 mg/kg body weight/day. Because of the low toxiicity of the compounds of the present invention larger doses can be administered, such as 8-12 mg/kg body weight/day.

The compounds of the present invention can be formulated by procedures well-known to those skilled in the pharmaceutical technology into the usual administration forms which comprise orally or parenterally administerable solid and liquid unit dosage forms. These unit dosage forms comprise from about 20 to about 100 mg of active principle, in addition to the usual excepients.

What is claimed is:

1. Compound having general formula (I)

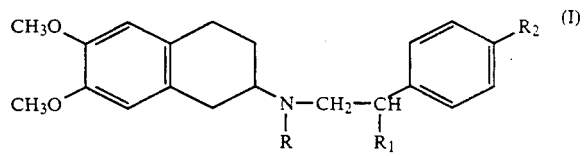

wherein:
R is selected from hydrogen, ethyl, n-propyl and methyl cyclopropyl;
$R_1$ is selected from hydrogen, hydroxy and —$OR_3$ wherein $R_3$ is selected from methyl, ethyl and n-propyl; and
$R_2$ is selected from hydrogen, methyl, hydroxy, trifluoromethyl, fluoro and methoxy.

2. As compound of claim 1, 2-[(N-methylcyclopropyl, N-p-methoxyphenylethanol)amino]-6,7-dimethoxy tetraline hydrochloride.

3. As compound of claim 1, 2-[(N-propyl,N-phenyl-2-ethanol)amino]-6,7-dimethoxy tetraline hydrochloride.

4. As compound of claim 1, 2-[(N-methyl cyclopropyl, N-phenyl-2-ethanol)amino]-6,7-dimethoxy tetraline hydrochloride.

5. As compound of claim 1, 2-[(N-propyl,N-2-p-methyl phenyl-2-ethanol)amino]-6,7-dimethoxy tetraline hydrochloride.

6. As compound of claim 1, 2-[(N-2-phenyl-2-ethanol)amino]-6,7-dimethoxy tetraline hydrochloride.

7. As compound of claim 1, 2-[(N-ethyl,N-2-phenyl ethyl)amino]-6,7-dimethoxy tetraline hydrochloride.

8. As compound of claim 1, 2-[(N-methyl cyclopropyl, N-p-methyl phenyl-2-ethanol)amino]-6,7-dimethoxy tetraline hydrochloride.

9. As compound of claim 1, 2-[(N-ethyl,N-2-p-methyl phenyl-2-ethanol)amino]-6,7-dimethoxy tetraline hydrochloride.

10. As compound of claim 1, 2-[(N-2-p-methyl phenyl-2-ethanol)amino]-6,7-dimethoxy tetraline hydrochloride.

11. As compound of claim 1, 2-[(N-ethyl, N-2-phenyl-2-ethanol)amino]-6,7-dimethoxy tetraline hydrochloride.

12. As compound of claim 1, 2-[(N-2-p-methoxy-phenyl-2-ethanol)amino]-6,7-dimethoxy tetraline hydrochloride.

13. As compound of claim 1, 2-[(N-2 phenyl-2-methoxy ethyl)amino]-6,7-dimethoxy tetraline hydrochloride.

14. As compound of claim 1, 2-[(N-2-p-trifluoromethylphenyl-2-ethanol)amino]-6,7-dimethoxy tetraline hydrochloride.

15. As compound of claim 1, 2-[(N-ethyl, N-2-p-trifluoro methyl phenyl-2-ethanol)amino]-6,7-dimethoxy tetraline hydrocloride.

16. As compound of claim 1, 2-[(N-2-p-fluoro phenyl-2-ethanol)amino]-6,7-dimethoxy tetraline hydrochloride.

17. As compound of claim 1, 2-[(N-2-p-hydroxyphenyl-2-ethanol)amino]-6,7-dimethoxy tetraline hydrochloride.

18. An orally or parenterally administrable pharmaceutical composition comprising an amount of a compound of claim 1 effective for reducing the pressure in a hypertensive patient, and a pharmacologically acceptable excipient therefor.

19. An orally or parenterally administrable pharmaceutical composition comprising an amount of a compound of any of the claims 2-17 effective for reducing the pressure in a hypertensive patient, and a pharmacologically acceptable excipient therefor.

20. A pharmaceutical composition according to claims 18 or 19, in unit dosage form, comprising from about 20 to about 100 mg of one of said compounds.

* * * * *